United States Patent [19]
Yamazaki et al.

[11] Patent Number: 5,485,398
[45] Date of Patent: Jan. 16, 1996

[54] METHOD AND APPARATUS FOR INSPECTING BENT PORTIONS IN WIRE LOOPS

[75] Inventors: Nobuto Yamazaki, Tachikawa; Shinichi Kumazawa, Higashikurume, both of Japan

[73] Assignee: Kabushiki Kaisha Shinkawa, Tokyo, Japan

[21] Appl. No.: 405,924

[22] Filed: Mar. 16, 1995

Related U.S. Application Data

[63] Continuation of Ser. No. 234,938, Apr. 28, 1994, abandoned, which is a continuation of Ser. No. 828,427, Jan. 31, 1992, abandoned.

[30] Foreign Application Priority Data

Jan. 31, 1991 [JP] Japan .................................. 3-029016

[51] Int. Cl.$^6$ .................................................... G01B 11/24
[52] U.S. Cl. ........................ 364/506; 364/560; 348/126; 382/146
[58] Field of Search ................... 364/489, 507, 364/552, 559, 560, 561, 506; 348/126, 136, 137, 142; 382/141, 146; 228/103, 104, 105; 33/1 BB; 356/237, 397

[56] References Cited

U.S. PATENT DOCUMENTS

| | | | |
|---|---|---|---|
| 3,846,008 | 11/1974 | Sobajima et al. | 356/247 |
| 4,445,633 | 5/1984 | Bonham, Jr. | 228/102 |
| 4,855,928 | 8/1989 | Yamanaka | 364/489 |
| 4,872,052 | 10/1989 | Liudzius et al. | 358/106 |
| 4,942,618 | 7/1990 | Sumi et al. | 382/8 |
| 4,980,763 | 12/1990 | Lia | 358/98 |
| 5,060,389 | 10/1991 | Frederick | 33/1 BB |
| 5,138,180 | 8/1992 | Yamanaka | 358/106 |
| 5,170,062 | 12/1992 | Miyahara | 250/561 |
| 5,298,989 | 3/1994 | Tsukahara et al. | 348/126 |
| 5,309,229 | 5/1994 | Stolz et al. | 348/128 |

*Primary Examiner*—Michael Zanelli
*Attorney, Agent, or Firm*—Koda and Androlia

[57] ABSTRACT

In inspecting a bend of a wire which is bonded to, for example, a semiconductor device, a straight scale line with scale markings of constant intervals and a bonded-point line, both lines crossing each other at right angles, are shown on a monitor. An image of a wire that has a bend is monitored by a camera and displayed on a monitor. By overlapping the image of the bend of the wire on the scale line and then reading a scale marking which is closest to the bend of the wire, it is possible to ascertain the amount of the bend of the wire.

3 Claims, 3 Drawing Sheets

METHOD AND APPARATUS FOR INSPECTING BENT PORTIONS IN WIRE LOOPS

This is a continuation of application Ser. No. 08/234,938, filed Apr. 28, 1994, now abandoned, which is a continuation division of application Ser. No. 07/828,427, filed Jan. 31, 1992, now abandoned.

BACKGROUND OF THE INVENTION

1. Field of the Invention

The present invention relates to a method and apparatus which inspect a bent portion of a wire bonded to, for example, semiconductor devices.

2. Prior Art

In the manufacture of semiconductor devices such as integrated circuits, etc., there is a wire bonding step. By the use of a wire bonding machine, wires 3, as shown in FIG. 4, are connected between the pads 1a of a pellet 1 and the leads 2a of a lead frame 2.

One example of a wire bonding machine is shown in FIG. 3.

The bonding machine 7 includes a bonding head 11 which is mounted on an XY table 10. The XY table 10 is driven in the X and Y directions by an X-axis motor 8 and a Y-axis motor 9. A bonding arm 12 is installed on the bonding head 11 and moved up and down by a Z-axis driver (not shown) that is installed in the bonding head 11. A bonding tool 13 is mounted at the tip end of the bonding arm 12, and a bonding wire (not shown) passes through this bonding tool 13. A camera holder 14 is mounted on the XY table 10, and a camera 15 is attached to this camera holder 14 with an off-set distance L between the camera 15 and the bonding tool 13. Workpieces are monitored by the camera 15, and the images of the workpieces are displayed on a monitor 17.

Workpieces are intermittently fed by a feeder 16, and the discrepancy between the position of each workpiece and a predetermined standard position is measured at least two points on a wire by the camera 15, and bonded point coordinate data is corrected in accordance with the measurement results. The distance L is added to the thus obtained corrected bonded point coordinate data, and the bonding tool 13 is moved accordingly, so that the bonding is performed onto the wires 3 as shown in FIG. 4.

In recent years, the distance between adjacent wires has generally becomes smaller as a result of increasing demand of fine pitch in semiconductor devices. As a result, there has been an increased danger of wires causing short circuits. For this reason, tolerance values of the bent portions (called "bends") in the wire loops have become extremely strict, and it is essential to measure and know exactly how large the bend of a wire loop is so that an adjustment is made accordingly in the wire bonding machine.

Conventionally, the bent portions in wire loops are inspected in the following manner: A workpiece with wires bonded to it is removed from a bonding machine and taken to a measuring instrument. As shown in FIG. 5, the distance S of the point 3c, which is the outermost point of the bend of the wire 3 between the first bonded point 3a and the second bonded point 3b from a straight line 4 which connects the first and second bonded points 3a and 3b, is observed and measured by microscopes. Since the maximum degree of bending is generally at the midpoint between two points (the first and second bonded points 3a and 3b in this case), the midpoint of the loop is selected as the outermost point 3c.

However, when the workpiece is removed from the bonding machine and taken to the measuring instrument, it might happen that the lead frame 2 is bent. If this occurs, the distances between the pads 1a of the pellet 1 and the leads 2a of the lead frame 2 change. This results in that the bend of the loop is further bent because the bent portion is pressed or elongated when the workpiece is bent.

Thus, according to the prior art inspection method, the bend of a wire loop is measured with an addition of the length caused by the deformation of the loop, and accurate measurements cannot be obtained. Furthermore, since the measurements are performed by hand, it requires a skilled operator and a long measurement time.

SUMMARY OF THE INVENTION

The object of the present invention is to solve the problems in the prior art and to provide a method and apparatus that inspect a bend in a wire loop with high accuracy, thus improving measurement precision and operating characteristics.

In the method of the present invention that achieves the object, a wire bonding machine, which includes an XY table that moves a bonding tool in X and Y directions, a camera that monitors the workpiece, and a monitor that displays the image of the wire obtained by the camera, is used. After wires are connected to a workpiece, at a bonding station of the bonding machine, the image of each of the wires connected is displayed on a monitor, a straight scale line with scale markings thereon are also displayed on the monitor, and then a point on the bend of the wire that crosses the scale line is read by counting the scale markings to know the size of the bend.

More specifically, on the display, the image of the loop of the wire, the scale line and a bonded-point line are displayed. The bonded-point line is a straight line drawn between two bonded points on a wire. The scale line is provided with scale markings at constant intervals and the bonded-point line crosses the scale line at right angles. The crossed point of those two lines is a measurement standard point (or a center mark). Image of the wire loop on the monitor is moved so that two bonded points on the wire come onto the bonded-point line. This brings the wire loop to cross the scale line. Then, a scale marking which is the closest to the crossing wire loop is read by counting them from the standard point. It is thus possible to know how large the bend of the wire loop is.

The apparatus of the present invention inspects, at a bonding station, a workpiece which has been wire-bonded. The inspection apparatus includes an XY table which moves a bonding tool in X and Y directions, a camera which monitors the workpiece, and a monitor which displays the image of the wire obtained by the camera. The apparatus further includes (a) a wire coordinate calculating section which calculates the measuring coordinates one the bonding point line which connects a first bonded point and a second bonded point of the wire, and (b) a scale marking coordinates calculating section which calculates the scale marking on the scale line which is perpendicular to the bonded-point line and crosses the summit of the loop of the wire. The monitor displays the scale line and the wire so that the distance between one of the scale markings which is the closest to the summit of the loop and a standard point which is the intersection of the bonded-point line and the scale line is calculated to know the data of the amount of the bend of a wire loop.

Since the bend in each wire loop is displayed on the monitor and measured at the bonding station, only those data which represent the bend of the wire loop is obtained. Also, since the scale markings are displayed on a straight scale line that is perpendicular to the bonded-point line which connects two bonded points of the wire, measurements can be performed by merely counting these scale markings. Accordingly, no special skill is required in measuring of bend of bonded wire, and the measurement takes only a short period of time.

DETAILED DESCRIPTION OF THE INVENTION

One embodiment of the present invention will be described below in detail with reference to the accompanying drawings.

Figure 1:
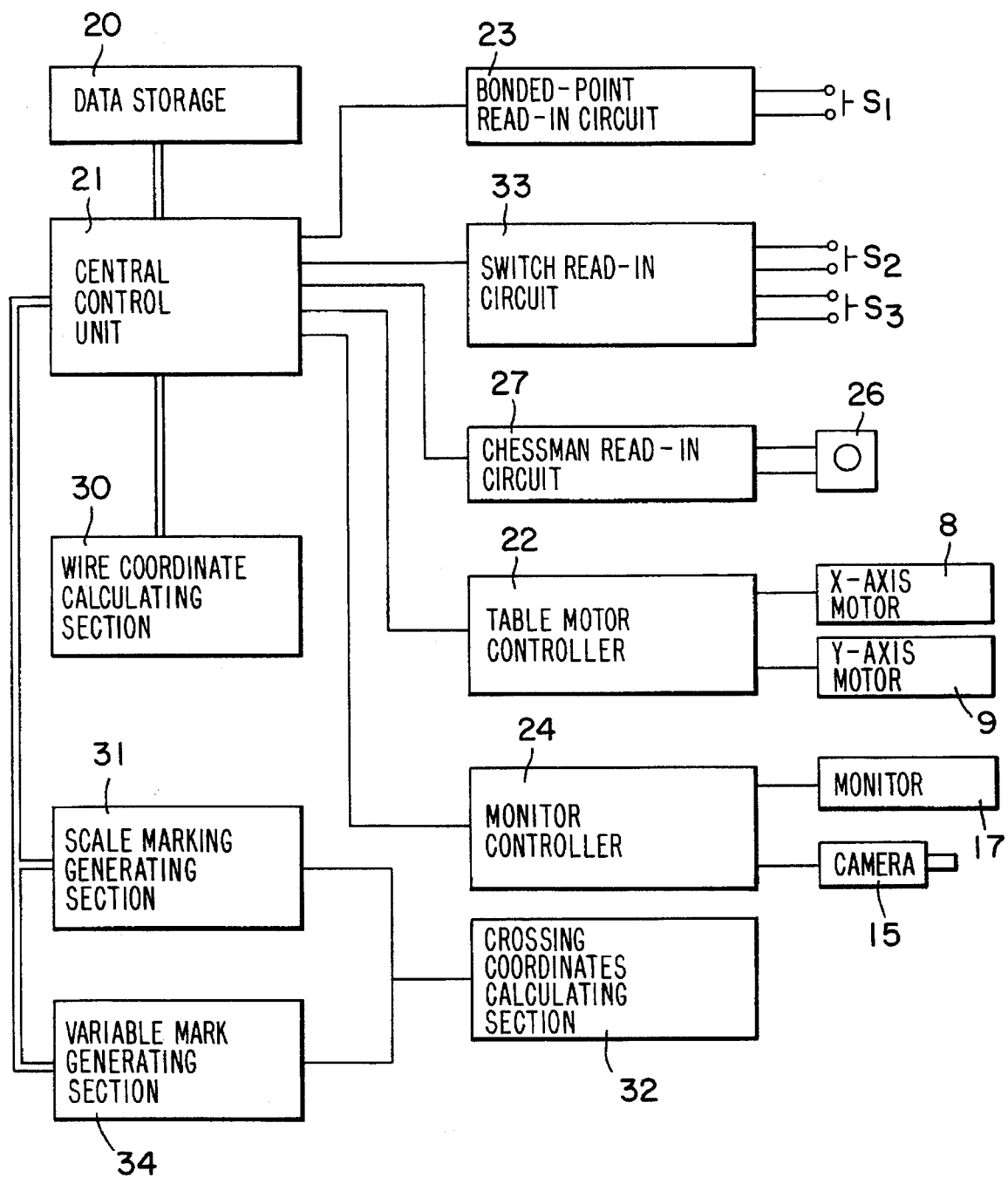
FIG. 1 is a block diagram representing the apparatus for inspecting bends in wire loops according to the present invention.

FIG. 1 shows a block diagram showing each element of the inspection apparatus of the present invention.

Figure 3:
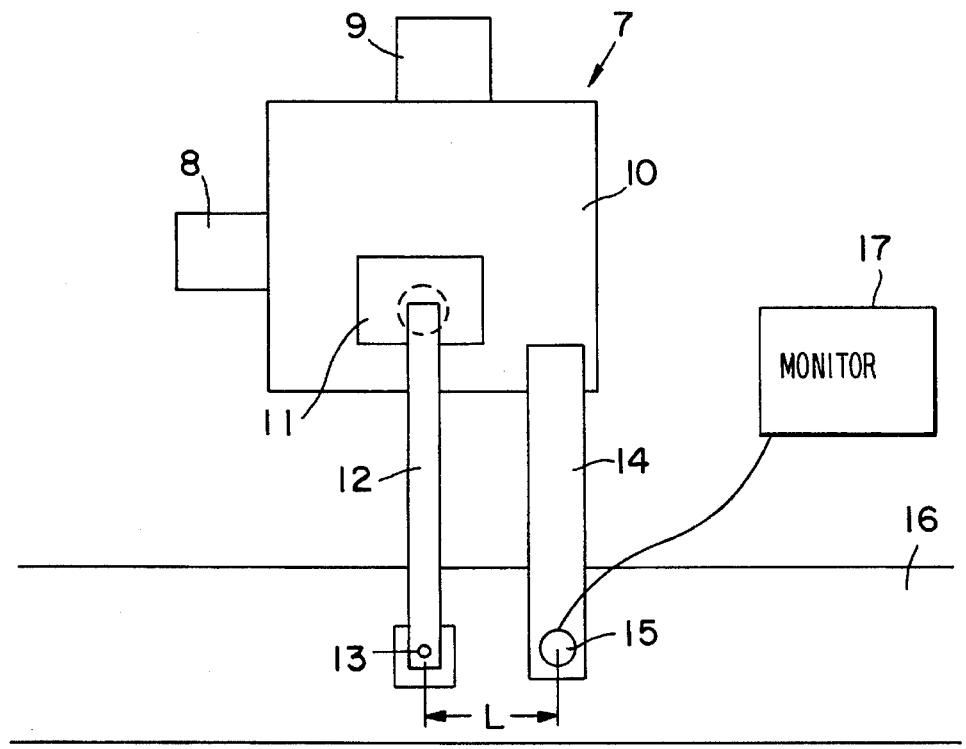
FIG. 3 is a schematic top view of a wire bonder used with the inspection apparatus of the present invention.
Figure 4:
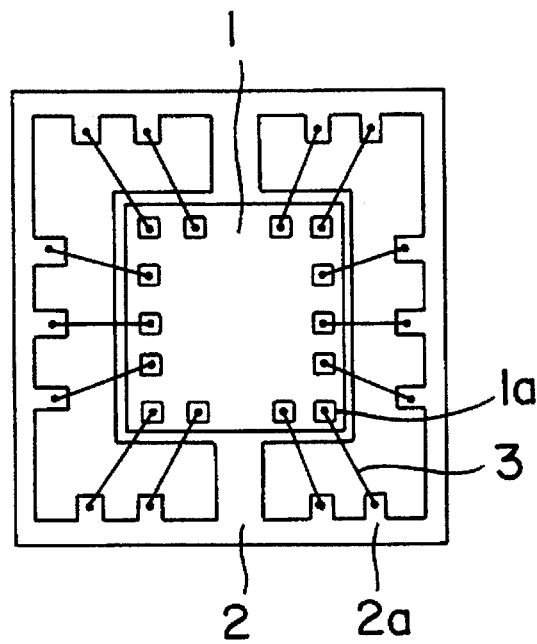
FIG. 4 is a top view of a wire-bonded workpiece.

Data of the bonded point coordinate is stored in a data storage 20. When a wire bonding is performed, data stored in the data storage 20 is read out by central control unit 21 and outputted to a table motor controller 22 which controls and drives an XY table. An X-axis motor 8 and a Y-axis motor 9 are driven by the table motor controller 22. Thus, the XY table 10 (shown in FIG. 3) is driven in the X and Y directions so that a bonding tool 13 is successively positioned above the bonding points of the wire. The bonding arm 12 is also moved vertically and bonding is successively performed between the pads 1a of a pellet 1 and the leads 2a of a lead frame 2 as shown in FIG. 4. Each one of the pads 1a represents the first bonded point, and each one of the leads 2a represents the second bonded point in the present invention which will be described in detail below. Since this bonding method is known in the prior art, further description will be omitted.

An inspection of a bend of the wire bonded to the workpiece will be described below.

Each time a bonded point call switch S1 shown in FIG. 1 is pressed, bonded point data stored in the data storage 20 is called up by the central control unit 21 via a bonded point read-in circuit 23. Then, the offset distance L (see FIG. 3) of the camera 15 is added to this read-out data, and a signal is outputted to the table motor controller 22 by the central control unit 21. As a result, the X-axis motor 8 and the Y-axis motor 9 are driven by the table motor controller 22 so that the XY table 10 is driven in the X and Y directions, causing the camera 15 to be successively positioned above the bonded points. In other words, bonded points of the wire to be measured are selected when the bonded point call switch S1 is pressed.

Figure 5:
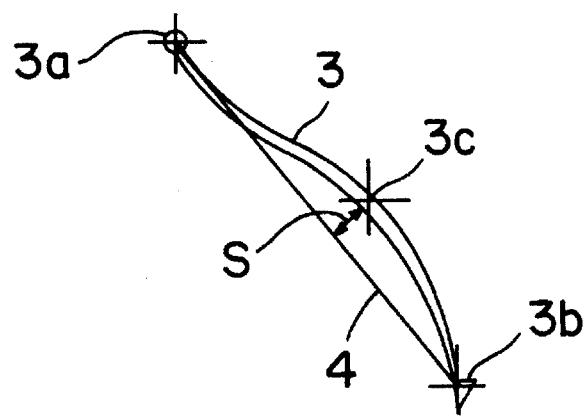
FIG. 5 is a top view of the bend of a wire being measured by the prior art method.

When the first bonded point 3a of the wire 3, that is to be measured and as shown for example in FIG. 5, is selected by pressing the bonded point call switch S1, the camera 15 is positioned above the first bonded point 3a, and the bonded point 3a is monitored by the camera 15. The image of this first bonded point 3a is displayed on the monitor 17 via a monitor controller 24. If the bonded point 3a is on a center mark of the monitor 17, the coordinate data of the bonded point 3a is sent "as is" to a bonded point read-in circuit 23. If there is a discrepancy between the image of the first bonded point 3a and the center mark of the monitor 17, a chessman 26 which is known in the prior art is operated, and the XY table 10 is driven to move the camera 15 so that the first bonded point 3a is aligned with the center mark of the monitor 17. The coordinates thus obtained are sent to a chessman read-in circuit 27. Coordinate data of the second bonded point 3b is inputted by the same operation as that performed for the first bonded point 3a. All the operations described above are accomplished by the conventional wire bonding machine 7.

In the present invention, as shown in FIG. 1, a wire coordinate calculating section 30, a scale marking generating section 31, a crossing coordinates calculating section 32, an increase conversion switch S2 for increasing the distance between scale markings, a decrease conversion switch S3 for decreasing the distance between scale markings, and a switch read-in circuit 33 used for the switches S2 and S3 which change the distance between the scale markings are utilized.

Figure 2:
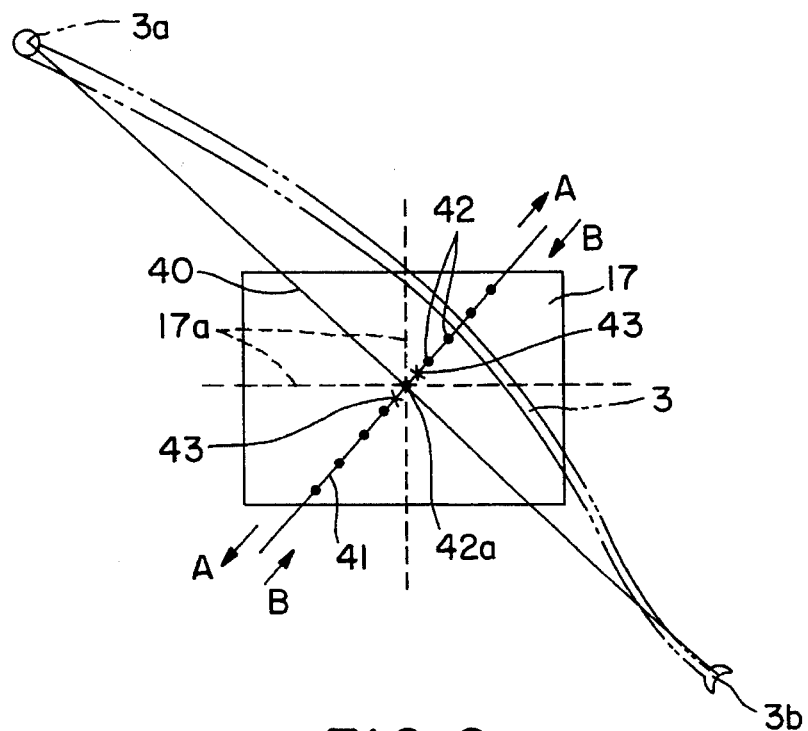
FIG. 2 is an explanatory diagram showing the monitor screen used in an inspection of a bend in a wire loop.

The wire coordinate calculating section 30 calculates the coordinates on a straight line (hereafter called "bonded-point line") 40 which connects the first bonded point 3a and the second bonded point 3b of the wire 3, as shown in FIG. 2. These coordinates of the two points are calculated on the basis of the coordinate data for the first bonded point 3a and coordinate data for the second bonded point 3b which are inputted as described above.

When the measurement of the bend in the wire loop is performed, the bonded point call switch S1 and chessman 26 function differently from what is described above. More specifically, when the bonded point call switch S1 or chessman 26 is operated, the XY table 10 is driven by the central control unit 21 on the basis of the coordinates calculated by the wire coordinate calculating section 30 so that the camera 15 moves only along the bonded-point line 40. In other words, as shown in FIG. 2, the bonded-point line 40 always crosses the center marks 17a of the monitor 17.

The crossing coordinates calculating section 32 calculates the coordinates of the scale markings 42 marked at constant intervals on a straight line (called "scale line") 41 which runs perpendicular to the bonded-point line 40. These coordinates are calculated based upon the coordinate data on the bonded-point line 40 which are calculated by the wire coordinate calculating section 30 and inputted from the central control unit 21 via the scale marking generating section 31. The scale markings 42 thus calculated by the crossing coordinates calculating section 32 are displayed in the following manner: By means of the scale marking generating section 31, a central scale marking 42a is displayed at a position that corresponds to the crossed point of the center marks 17a of the monitor 17, and a plurality of scale markings 42 are marked on the scale line 41 so that an equal number of markings appear on both sides of the central scale marking 42a.

Thus, the amount of bend in the wire is measured by counting the number of scale markings 42 between the wire 3 and the central scale marking 42a. The distance between the scale markings 42 is fixed at, for example, 50 microns, 100 microns, etc. The values 50 microns and 100 microns referred to here are, however, not the distances on the screen of the monitor 17 but are the actual measuring distances.

If the distance of the scale markings 42 is set at 50 microns in FIG. 2, then, since the wire 3 is located between the second scale marking and the third scale marking from the standard central scale marking 42a, the amount of bend in the wire 3 is judged to be approximately 120 microns, which is between 100 and 150 microns.

Thus, since the bend in each wire loop is measured at the bonding station by displaying the image of the wire loop on the monitor 17, data that represents only the bend in the wire loop is obtained. Furthermore, since the scale markings 42 are displayed on the scale line 41 which runs perpendicular to the bonded-point line 40 (that connects the first bonded point 3a and second bonded point 3b), measurements can be made merely by reading these scale markings 42. Accordingly, no skill is required, and measurements are performed easily in a short period of time.

As shown in FIG. 1, the inspection apparatus of the present invention further includes a variable mark generating section 34 so as to perform more accurate measurements of the bend. In other words, with the variable mark generating section 34, it is possible to inspect the bend more accurately when the wire loop is between two markings.

The variable mark generating section 34 displays, on the monitor 17, a variable mark 43 which is moved at a desired pitch on the scale line 41 which is calculated by the crossing coordinates calculating section 32. For convenience of illustration, the variable mark 43 is indicated by an "X" in FIG. 2. In actuality, however, this mark 43, like the scale markings 42, is shown as a dot on the monitor. Furthermore, the distance the variable mark 43 moves from the central scale marking 42a and the pitch at which the variable mark 43 moves each time may be displayed in numerical values on the monitor 17.

The variable mark 43 is moved one pitch at a time in the plus or minus direction on the scale line 41 when the increase conversion switch S2 or the decrease conversion switch S3 is pressed. The plus direction is the direction shown by arrows A and the minus direction is the direction shown by arrows B in FIG. 2. The pitch by which the variable mark 43 moves each time can be changed to, for example, 2.5 microns, 5 microns, etc., by adjusting the increase conversion switch S2 or the decrease conversion switch S3.

Accordingly, as shown in FIG. 2, the bend in the wire can be more accurately measured by operating the increase conversion switch S2 or the decrease conversion switch S3 so that the variable mark 43 is moved on the scale line 41 until it comes onto the measurement point of the wire 3.

In the present invention, as described above, a bend in the wire loop is measured at the bonding station by viewing the image of the wire loop on a monitor. As a result, the precision of measurement is high. Furthermore, since the scale markings are displayed on a straight line that is perpendicular to a bonded-point line which Connects the first and second bonded points, measurements can be made merely by reading or counting these scale markings, thus improving the working characteristics.

We claim:

1. An apparatus for inspecting a bend in a wire loop after wires are connected to a workpiece at a bonding station of a wire bonding machine wherein said wire bonding machine includes an XY table with a bonding tool provided thereon, through which said wire is passed, a camera for monitoring an image of a selected one of said connected wires of said workpiece, said camera being mounted on said XY table and said camera and bonding tool being moved in X and Y directions by said XY table and a monitor for displaying said image obtained by said camera, said inspection apparatus comprising: a wire coordinate calculating means for calculating coordinates of a first bonded point and a second bonded point of said selected one of said connected wires, said coordinates of said first and second bonding points for determining a bonded point line which is a straight line connecting said first and second bonded points; and crossing coordinates calculating means for calculating scale markings on a straight scale line passing through a center point of said monitor, said scale line being perpendicular to said bonded point line, said scale markings corresponding to predetermined actual measuring distances on said workpiece; and a scale marking generating means for displaying said scale markings of said scale line on said monitor along with said selected one of said connected wires to be measured to visually measure said bend in said wire loop accurately by counting the number of scale markings between said wire loop and the center point without moving the workpiece from the bonding station.

2. An apparatus according to claim 1, further comprising a variable mark generating means for calculating and generating a variable mark on said scale line, said variable mark stepwise movable on said scale line a predetermined distance less than a distance between two successive scale markings whereby said bend in said loop can be more accurately measured.

3. A method of inspecting a bend in a wire loop after wires are connected to a workpiece at a bonding sight of a wire bonding machine wherein said wire bonding machine includes an XY table with a bonding tool provided thereon, a camera which monitors an image of said workpiece, said camera being mounted on said XY table and said camera and bonding tool being moved in X and Y directions by said XY table and a monitor which displays said image obtained by said camera, said inspection method comprising the steps of: displaying an image of a selected one of said connected wires on said monitor at a bonding station; calculating coordinates of a first bonding point and a second bonding point of said selected one of said connected wires; determining a bonded point line from said coordinates of said first and second bonding points, said bonded point line being a straight line connecting said first and second bonding points; calculating scale markings on a straight scale line passing through a center point of said monitor, said scale line being perpendicular to said bonded point line and said scale markings corresponding to predetermined actual distances on said workpiece; displaying said scale markings on said scale line on said monitor along with said selected one of said connected wires to be measured to visually measure said bend in said wire loop accurately by counting the number of scale markings between said wire loop and the center point without moving said workpiece from the bonding station.

* * * * *